Figure 1:
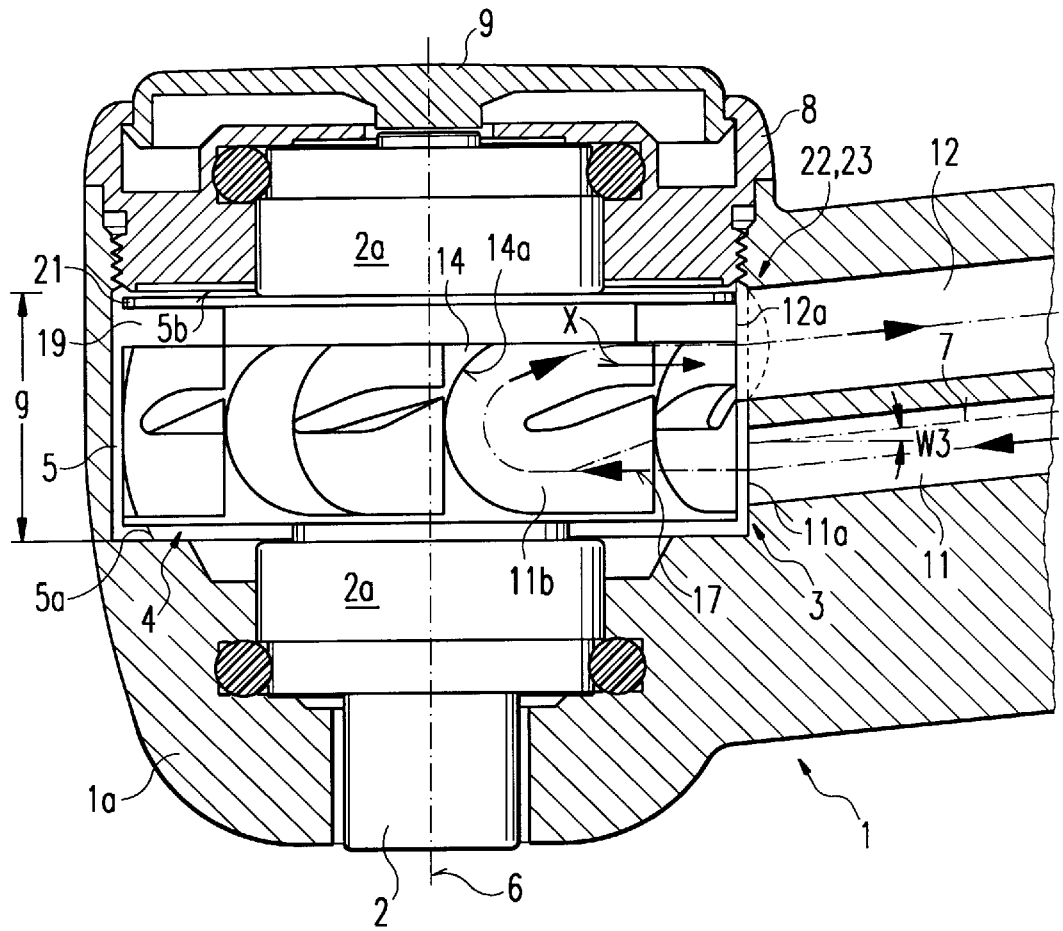

United States Patent
Bareth et al.

[11] Patent Number: 6,120,291
[45] Date of Patent: Sep. 19, 2000

[54] TURBINE HANDPIECE

[75] Inventors: Erich Bareth; Eugen Mohr, both of Ummendorf, Germany

[73] Assignee: Kaltenbach & Voigt GmbH & Co., Biberach/RiB, Germany

[21] Appl. No.: 09/358,307

[22] Filed: Jul. 21, 1999

[30] Foreign Application Priority Data

Jul. 23, 1998 [DE] Germany .............. 198 33 249

[51] Int. Cl.[7] .................................................. A61C 1/05
[52] U.S. Cl. ................................................ 433/132
[58] Field of Search ....................... 433/132; 415/904

[56] References Cited

U.S. PATENT DOCUMENTS

| | | | |
|---|---|---|---|
| 5,158,456 | 10/1992 | Lilley ........................... | 433/116 |
| 5,334,013 | 8/1994 | Meller .......................... | 433/132 |
| 5,340,312 | 9/1998 | Murase ......................... | 433/132 |
| 5,496,173 | 3/1996 | Wohlgetmuth ................ | 433/132 |
| 5,507,642 | 4/1996 | Wohlgemuth .................. | 433/132 |
| 5,562,446 | 10/1996 | Matsui et al. ................. | 433/132 |
| 5,567,154 | 10/1996 | Wohlgemuth .................. | 433/132 |
| 5,782,634 | 7/1998 | Lingenhöle et al. .......... | 433/132 |
| 5,807,108 | 9/1998 | Schwenoha et al. .......... | 433/132 |

FOREIGN PATENT DOCUMENTS

| | | |
|---|---|---|
| 43 38 243 | 5/1994 | Germany . |
| 44 28 039 C1 | 11/1995 | Germany . |
| 195 29 688 A1 | 2/1997 | Germany . |

OTHER PUBLICATIONS

European Search Report, Jan. 8, 1999.

*Primary Examiner*—Nicholas D. Lucchesi
*Attorney, Agent, or Firm*—Marshall, O'Toole, Gerstein, Murray & Borun

[57] ABSTRACT

The invention relates to a turbine handpiece (1), in particular for medical or dental-medical purposes, having a drive shaft (2), rotatably mounted in the forward end region of the handpiece (1), with which a tool can be connected by a mounting device, whereby there is arranged on the drive shaft (2), fixed for rotation therewith, a turbine wheel (4) in a turbine chamber (5), in which a delivery line (11) for a flowing pressure medium opens at an inlet opening (11a) and from which a discharge line (12) extends at an outlet opening (12a), whereby a apparatus (22) is provided which after a switching-off of the pressure medium supply, during the running on of the turbine wheel (4), prevents a release of the pressure medium rotating in the turbine chamber (5) through the discharge line. The latter is simplified and improved in that the apparatus (22) is arranged in the region of the turbine chamber (5) and in functional operation deflects the pressure medium rotating in the turbine chamber (5) past the outlet opening (12a).

18 Claims, 5 Drawing Sheets

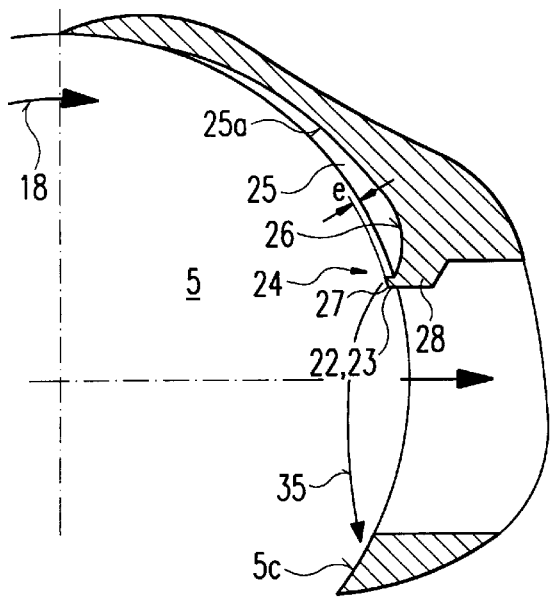
Fig. 8
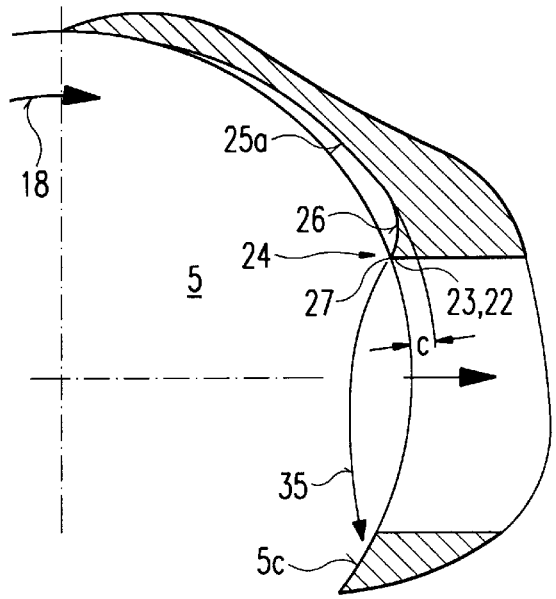
Fig. 9
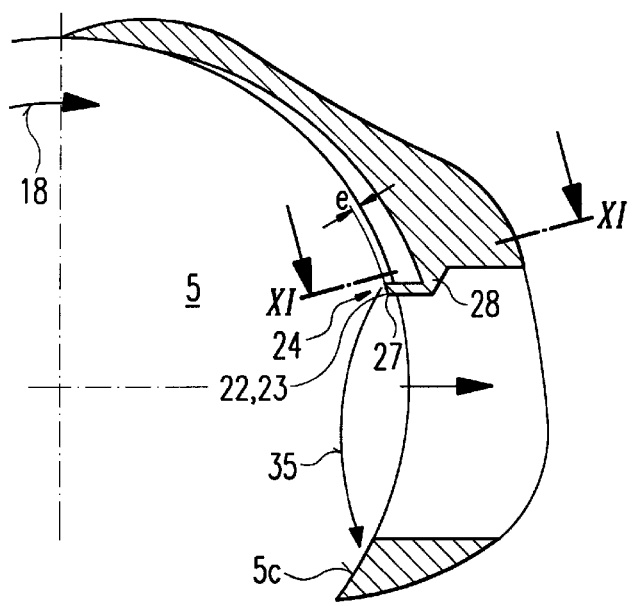
Fig. 10
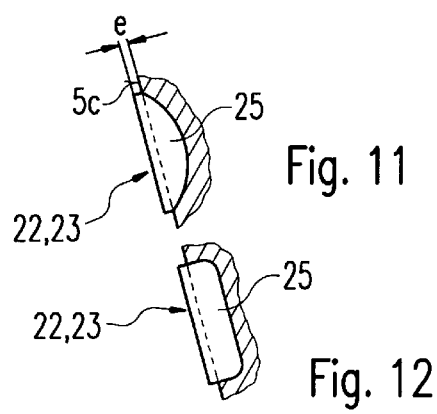
Fig. 11
Fig. 12

TURBINE HANDPIECE

The invention relates to a turbine handpiece particularly for medical or dental-medical purposes, having a rotatable drive shaft mounted in a forward end region of the end piece, with which a tool can be connected by means of a mounting device, with a turbine wheel in a turbine chamber disposed on the drive shaft for rotation therewith, in which a delivery line for pressure medium flowing from a supply opens at an inlet opening and from which a discharge line extends at an outlet opening, whereby means are provided preventing release of the pressure medium to a discharge line during operation of the turbine wheel after the pressure medium supply has been switched off.

In medical or dental-medical treatment stations, and also in medical or dental-medical laboratories, handpieces with two kinds of main drive have established themselves; namely on the one hand so-called motor handpieces, the drive shaft of which for the tool is driven with an electric motor, and turbine handpieces, the drive shaft of which stands in drive connection through a turbine arranged in the forward end region of the handpiece, which turbine is driven with a pressure medium, in particular compressed air. The invention relates to a handpiece of the latter kind.

With such a turbine handpiece, a turbine wheel is freely rotatably mounted in a substantially round turbine chamber. The pressure medium is delivered through a delivery line extending longitudinally in the handpiece, which flows through an inlet opening in the turbine chamber onto the turbine wheel, sets the turbine wheel in rotation and leaves the turbine chamber through an outlet opening and a discharge line adjoining thereon. The drive of the turbine is switched off by means of the closing of a valve in the delivery line. Since the handpiece is driven with very high speeds of rotation, the turbine wheel runs on for a considerable time after switching off of the pressure medium supply, whereby it compresses the pressure medium out of the turbine chamber into the discharge line and thus works as a pump. As a result of the partial vacuum thereby arising in the turbine chamber there is generated a suction effect inter alia in air gaps in the region of the tool mounting. This is undesired, since infection agents can be sucked into the handpiece, where disinfection is only inadequately possible or not possible at all.

In order to avoid the above-described sucking-in or sucking-back effect there has been developed in accordance with DE 195 29 668 A1 a handpiece of the kind indicated in the introduction, in the discharge line of which there is arranged a blocking valve which by means of the pressure of the delivered pressure medium is controlled to open and after a switching off of the pressure medium supply self-actingly closes, so that the turbine cannot carry out a pump function. This known handpiece has proved to be an advantageous solution in practice, but the arrangement of a switchable blocking valve is complicated and costly.

The object of the invention is to find a simple and economical configuration for the prevention of the pump function or of the sucking-in or sucking-back.

This object is achieved by disposing the means for preventing release of the pressure medium in the region of the turbine chamber whereby, in functional operation, the means deflects the pressure medium rotating in the turbine chamber past the outlet opening.

With the handpiece in accordance with the invention, there is arranged in the region of the turbine chamber a means preventing the sucking-in, which in functional operation of the handpiece deflects the pressure medium rotating in the turbine chamber past the outlet opening. By these means, the pressure medium is prevented from exiting through the outlet opening. Thus, also during running on of the turbine wheel after the switching off of the pressure medium supply, no pump function can take place and thus neither can a partial vacuum arise in the turbine chamber nor a sucking-in take place. The function in accordance with the invention is based on the rotating pressure medium flow in the turbine chamber forming, as it were, a curtain extending in front of the outlet opening which prevents the exit of the pressure medium through the outlet opening. The invention is thus based on the insight that the rotating pressure medium itself can form a "closure" of the outlet opening when it is deflected past the outlet opening. Here, there may be involved a laminar flow or also a zone of turbulence. Of significance is that in the region of the outlet opening the flow takes a path on which it prevents itself from exiting through the outlet opening. The achievement of this goal is simplified in that the pressure in the rotating pressure medium in the turbine chamber after switching-off corresponds largely to room pressure and thus is substantially "pressureless" and therefore even a relatively weaker flow curtain in front of the outlet opening can prevent exit therethrough. The flow deflection striven for can be attained by means of a flow step projecting into the flow which forces the rotating pressure medium, thus standing under centrifugal force, to take a flow path which is offset inwardly, whereby the flow has already passed the outlet opening when the flow offset caused by the step is no longer present. The functioning of the step in accordance with the invention can be compared with a ski jump, if the space present behind the jump edge is considered as outlet opening. Since the medium to be deflected past the outlet opening is a gas, in particular compressed air, it is to be assumed that an absolute flow curtain closure can hardly be achieved. However, tests have shown that a flow deflection inwardly, from the previous flow direction, in accordance with the invention has prevented an exit of the pressure medium through the outlet opening to such an extent that a harmful partial vacuum does not build up in the turbine chamber and that the sucking-in or sucking-back is effectively prevented.

Moreover, the invention has the purpose of improving the functioning and/or efficacy with a turbine handpiece.

The object is achieved by providing the inlet opening offset toward one side with regard to the radial middle plane of the turbine chamber, and by providing that the blades of the turbine wheel are bound on that side by an opposed sidewall of the turbine chamber, while providing play for movement, and directing the pressure medium axially to the other side into an annular chamber which lies radially opposite the outlet opening.

With this configuration in accordance with the invention, the pressure medium flows through the turbine blades axially, whereby behind the blades it can expand in an annular chamber out of which it can flow via the outlet opening. With such a configuration an advantageous flow path is predetermined along which the pressure medium encounters a relatively lesser flow resistance. By these means both running of the turbine and also the capacity of the turbine handpiece is improved. Further, this configuration in accordance with the invention is of a simple and economically manufacturable configuration, whereby the manufacture can be simplified and more economically carried out.

Preferred embodiments of the invention provide to further simple and economically manufacturable, and compact, constructions, which with the predetermined constricted space relationships lead to effective advantages.

Figure 2:
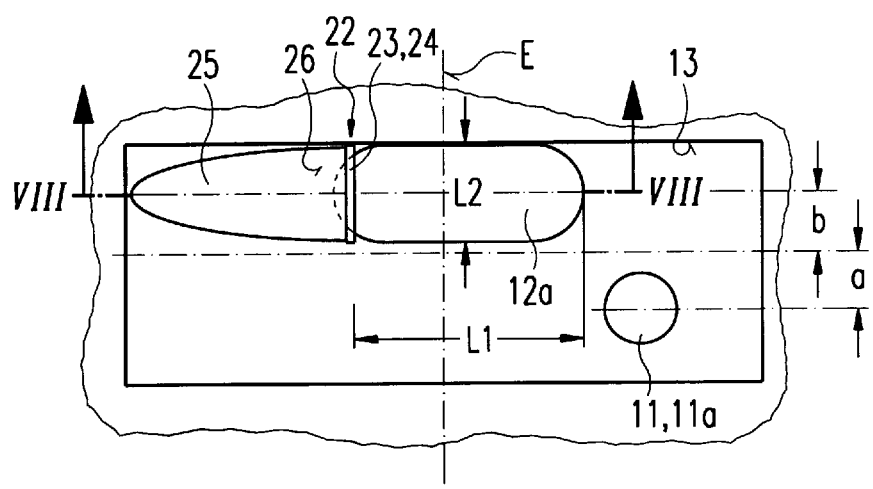
Figure 3:
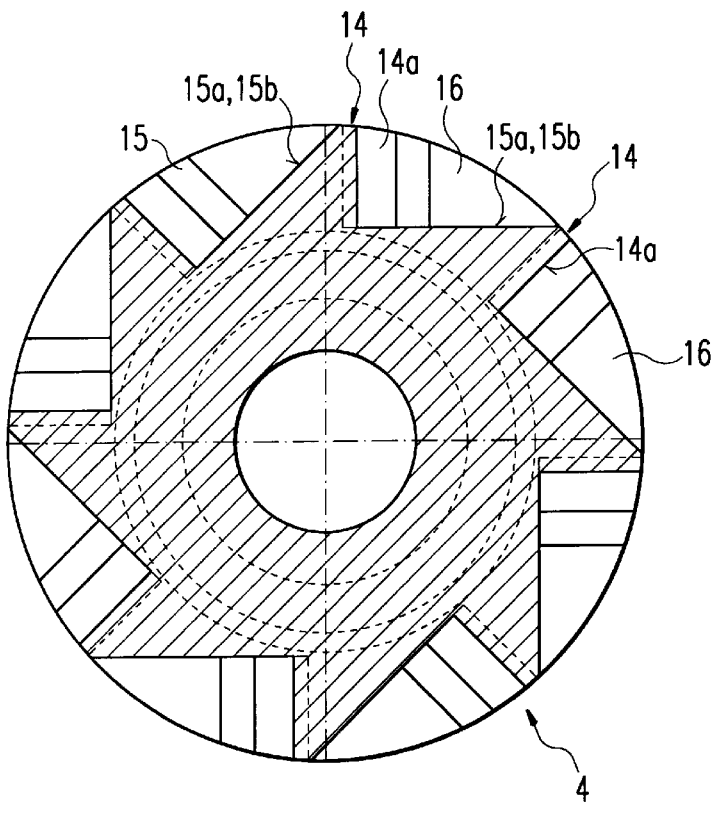
Figure 4:
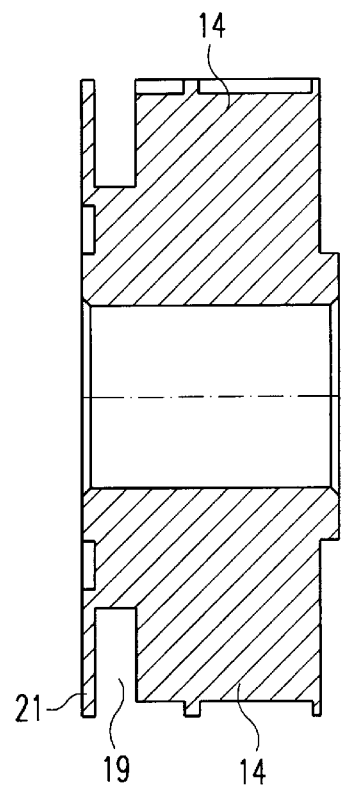
Figure 5:
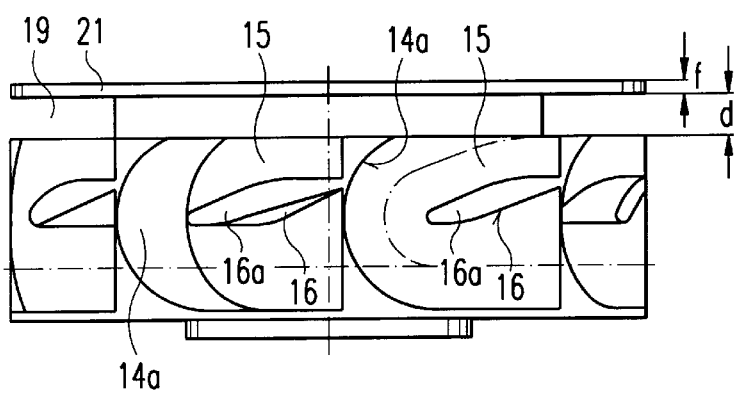
Figure 6:
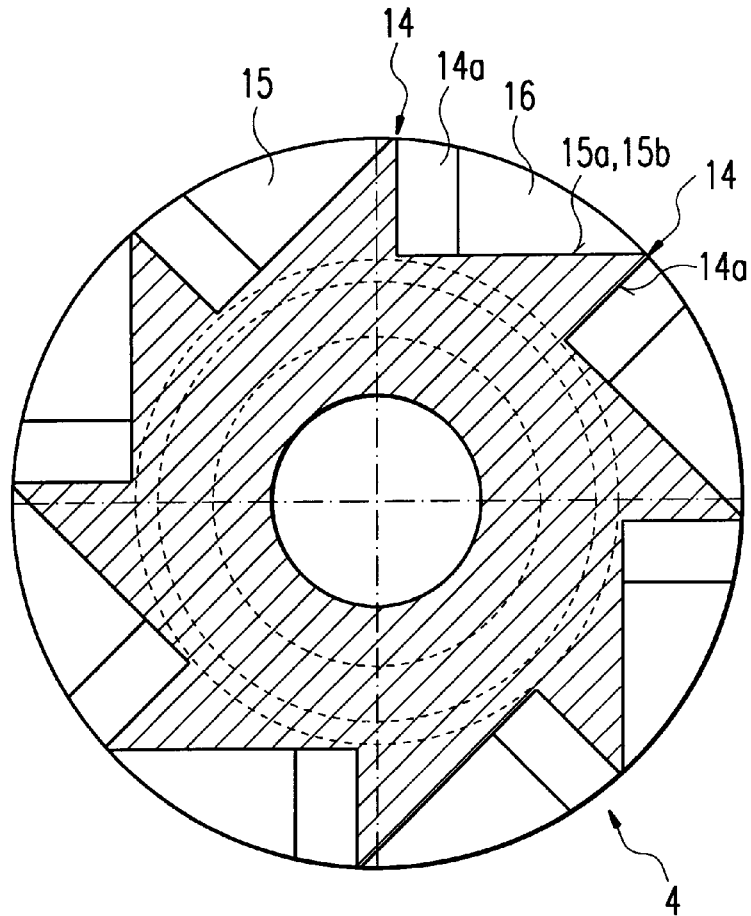
Figure 7:
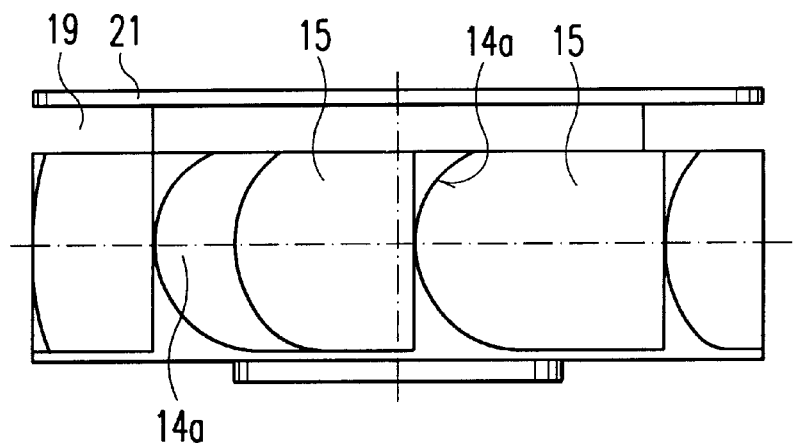

Below, the invention and further advantages which can be achieved thereby will be described in more detail with reference to advantageous exemplary embodiments and the drawings, which show:

FIG. 1 the forward end region of a handpiece in accordance with the invention, in axial vertical section;

FIG. 2 a detail of the handpiece in the direction of view indicated with an arrow X in FIG. 1, in an enlarged representation;

FIG. 3 a turbine wheel in diagonal section;

FIG. 4 the turbine wheel in axial section;

FIG. 5 the turbine wheel in a view from above;

FIG. 6 a turbine wheel of modified configuration, in diagonal section;

FIG. 7 the turbine wheel according to FIG. 6 in a view from above;

FIG. 8 the partial section VIII—VIII of FIG. 2;

FIG. 9 the partial section VIII—VIII in a modified configuration;

FIG. 10 the partial section VIII—VIII in a further modified configuration;

FIG. 11 the partial section XI—XI of FIG. 10

Figure 13:
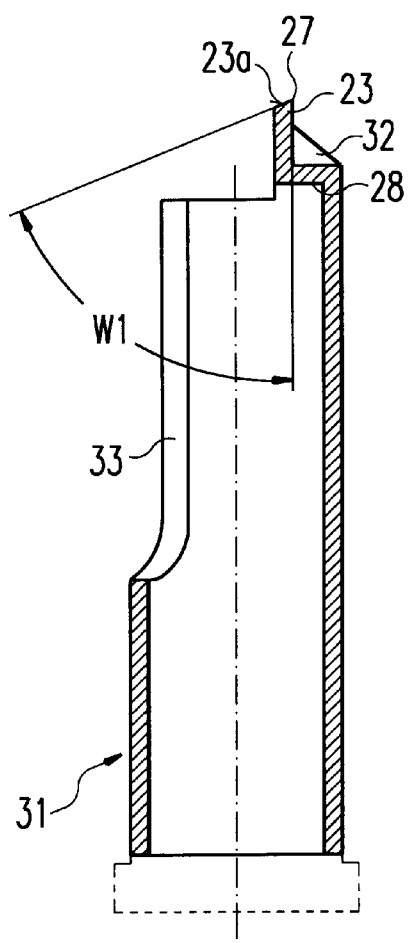
Figure 14:
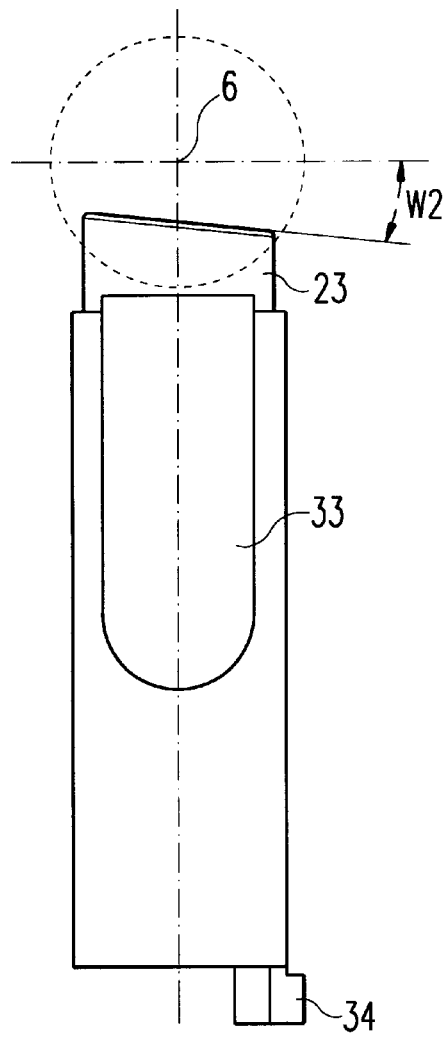
Figure 15:
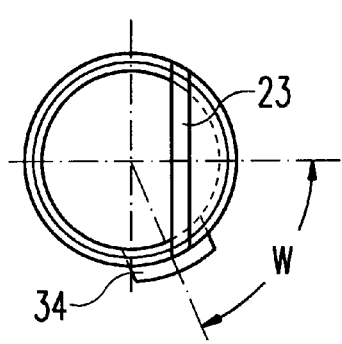

FIG. 12 the partial section XI—XI in a modified configuration;

FIG. 13 a particular configuration in accordance with the invention, on an insertion sleeve;

FIG. 14 the insertion sleeve in a side view from the left;

FIG. 15 the insertion sleeve in a view from the end.

The handpiece 1 is a rod-like grip body which, with its non-illustrated rear end, can be coupled to a so-called connection part which is connected with a flexible supply line for drive energy and auxiliary media, as is conventional. In the forward end region of the handpiece 1 a drive shaft 2 for a tool is rotatably mounted in a chamber, whereby the non-illustrated tool can be connected with the drive shaft 2 by means of a connection or mounting device likewise not illustrated in detail. For this purpose, the drive shaft 2 penetrates through a hole in a head housing 1a of the handpiece 1, so that the tool can be inserted from the outside into the hollow plug-in fitting drive shaft 2. The drive shaft 2 is drivable by means of a turbine 3, the turbine wheel 4 of which is arranged to rotate fixedly with the drive shaft 2, preferably being manufactured in one piece with the drive shaft, and is freely rotatable mounted in a turbine chamber 5 with play for movement on all sides, which chamber has a circular basic cross-sectional form. To the two sides of the turbine wheel 4 there are arranged on the drive shaft 2 bearing parts 2a, which are formed as sliding bearings or roller bearings and are mounted and sealed in the handpiece.

With the present configuration, the rod-form of the handpiece 1 extends straight or, in a manner known per se, angled (angled piece), whereby the axis of rotation 6 of the drive shaft 2 extends transversely of the longitudinal middle axis 7 of the handpiece body in the sense of a so-called angled head. The drive shaft 2 with the turbine wheel 4 is arranged to be mountable and removable from the side away from the tool. For this purpose, on that side the housing 1a is closed by a threaded plate 8 on which a pressure button 9 is mounted with which the tool can be released from the non-illustrated tool mounting device.

The turbine 3 is driveable by means of a pressure medium, in particular compressed air. For the delivery and discharge there serve a delivery line 11 and a discharge line 12, which extend longitudinally through the handpiece body and by means of the above-mentioned connection coupling are connectable to further delivery and discharge line sections running in the supply line.

The delivery line 11 opens at an inlet opening 11a into the turbine chamber 5, which opening with regard to this turbine chamber develops with the opening section of the delivery line 11 secantially and in the present exemplary embodiment is arranged offset axially off-centre; see offset amount a. The discharge line 12 extends from an outlet opening 12a which has a greater cross-sectional area than the cross-sectional area of the inlet opening 11a and is offset to the other side by the offset amount b, preferably so far that it is bounded by the associated side edge 13 of the turbine chamber 5. With the present configuration, the outlet opening 12a has the form of an elongate hole with semi-circularly rounded elongate hole ends, which with regard to a longitudinal middle plane E containing the axis of rotation 6 is approximately centrally arranged. The length L1 of the longitudinal hole or of the outlet opening 12a, running transversely to the axis of rotation 6, is greater than the axial dimension L2. Seen transversely to the longitudinal middle plane E, the openings 11a, 12a and the delivery and discharge lines 11, 12 are arranged one above another, whereby the outlet opening 12a and the discharge line 12 are at the top.

The turbine wheel 4 can be formed in one piece with the drive shaft 2, whereby it is formed in substance by means of a cylindrical body which at its periphery has a plurality of blades 14 having blade surfaces 14a extending transversely to the longitudinal direction of the handpiece 1 which preferably, with regard to the incoming flow direction, are formed as concave cylindrical section shaped surfaces, which are bounding surfaces from angle-shaped recesses 15 arranged in the envelope surface, the in particular planar base surfaces 15a of which, apart from the concave shape of the blade surfaces 14a, run out to both sides and in each case form a rear surface 15b of the preceding blade 14. With the configuration in accordance with FIGS. 1 and 3 to 5 there are arranged before the respective blade surfaces 14a respective middle webs 16 each of which extends from the base surface 15a radially outwardly and ends at the imaginary cylindrical outer envelope of the turbine blade 4, so that also the envelope surface section 16a of the middle web 16 is located in the cylindrical envelope. Seen in the view from above, the middle webs 16 are located approximately in a middle transverse plane of the turbine wheel 7, whereby the inlet opening 11a is arranged approximately in alignment with an inlet channel 11b present between the middle webs 16 and the associated side wall 5a of the turbine chamber 5. The middle webs 16 extend in peripheral direction, with regard to the incoming flow direction 17, convergently or obliquely with rounded web tips facing in the direction of rotation 18, whereby the power of the turbine 3 is increased. The middle webs 16 bring about a directing of the pressure medium flow onto the one side of the blade surfaces 14a, whereby the pressure medium flows through the blades 14 at the rounded blade surfaces 14a.

On the other side of the turbine wheel 4 there is arranged an annular chamber 19 in the turbine wheel 4, which is located in the region of the outlet opening 12a and which may be formed by means of a recess open radially and at the end or by means of an annular groove, if appropriate in the vicinity of the end, whereby the annular chamber 19 is bounded towards the end by a thin turbine wheel web 21 which is part of the turbine wheel body and cooperates, with play for movement, with the neighbouring side wall 5b of the turbine chamber.

The turbine wheel 4 according to FIGS. 6 and 7 differs from the turbine wheel 4 according to FIGS. 3 to 5 in that the middle webs 16 are omitted. Such a turbine wheel 4 is also capable of functioning.

There is associated with the turbine 3, in the region before the outlet opening 12 in the direction of rotation 18, a means 22 which in functional operation of the turbine 3 deflects the pressure medium rotating in the turbine chamber 5 in the direction of rotation 18 past the outlet opening 12a. The means 22 is formed by a flow web 23 projecting into the flow path, which is arranged in the region of the first edge 24—with reference to the flow direction 18—of the outlet opening 12a and deflects the flow from the outlet opening 12a inwardly, so that this first reaches the peripheral wall 5c of the turbine chamber 5 behind the outlet opening 12a. Functionally, the web 23 is comparable with a ski jump at which the flow over the outlet opening 12a is lifted and thereby is prevented from exiting through the outlet opening 12a. Since the amount c, with which the web 23 projects into the rotating pressure medium flow as flow step, can be greater than the radial spacing between the peripheral wall 5c of a turbine chamber 5 and the turbine wheel 4, there is arranged in the peripheral wall 5c, in alignment with the available width L2 of the outlet opening 12a, a flow groove 25 which is sunk flat into the peripheral wall 5c and in accordance with FIGS. 8 and 9 runs out with a strongly concave rounding to the edge 24 and forms a deflection surface 26, whereby the web 23 is formed. The base surface of the flow groove 25 has approximately the form of a parabola having a concave curvature increasing in the flow direction to the break-off edge 27. With the present configuration, the flow groove 25 begins in the region of the Y-axis of the associated cross-sectional quadrant, the X-axis of which runs through the outlet opening 12a. It is advantageous to allow the rounded deflection surface 26 of the flow groove 25 to run out at a sharp edge of the web 23 in order to attain a disruption-free break-off of the flow at the break-off edge 27. Thereby it is further advantageous if the web 23 extends straight. Since, however, the edge 24 of the round outlet opening 12a and the flow web 23 in accordance with FIG. 9 develop in a curved arc-form and thus a web 23 extending in a straight manner is not realisable, in accordance with FIGS. 2, 8 and 10—in which the same or similar parts are provided with the same reference signs—a web 23 is proposed which with reference to the actual edge 24 of the outlet opening 12a is offset towards the centre of the opening and so that it extends secantially of the rounded hole cross-sectional form. In order to make this offset possible, the flow web 23 is arranged on a base web 28 which carries the flow web 23 and which is formed in one piece with the flow web 23 on the body of the housing 1a.

The configuration according to FIG. 10, in which the same or similar parts are provided with the same reference signs, differs from the configuration according to FIG. 9 solely in that the deflection surface 26 rising ramp-shaped to the flow web 23 is omitted. Instead of this deflection surface 26, the base surface 25a of the flow groove 25 extends further in circular arc-shape up to a boundary formed as a thin flow web 23.

As can be recognised from FIGS. 11 and 12, the cross-sectional form of the flow groove 25 can have various shapes. With the configuration according to FIG. 11 there is provided a circular section-shaped cross-sectional form. With the configuration according to FIG. 12 there is provided a right-angle shaped cross-sectional form, whereby the edges are preferably rounded.

With the configuration according to FIGS. 13 to 15, in which the same or similar parts are provided with the same reference signs, differs from the above-described exemplary embodiments in that the flow web 23 is arranged not on the body of the housing 1a or handpiece 1 but on a sleeve or bushing 31, which is fixedly emplaced so far into the discharge channel 12 that the flow web 23 projects over the base surface 25a of the flow groove 25 and is located at or in the vicinity of the edge 24. With the present configuration there is provided a thin sheet bushing which at its forward end has the flow web 23 secantially inwardly offset, which flow web is arranged on a circular arc section shape end wall which forms the base web 28. The flow web 23 can be stabilized by means of a so-called gusset plate 32. In the peripheral region of the bushing 31 lying opposite to the flow web 23 there is provided a recess or slit opening 33 which in particular in the case of a broader outlet opening 12a ensures the broadening. At the rear edge of the bushing 31 there may be provided at least one radially projecting edge angle 34 which can form a stop for bounding the displacement of the bushing 31 inwardly and/or can provide rotational securing, and with regard to the longitudinal plane containing the slit opening 33 may be arranged rotated by an angle W of about 60°.

As shown clearly particularly in FIG. 13, the end surface 23a of the flow web 23 can be undercut by means of a free angle so that the wedge angle W1 of the flow web 23 is about 50 to 85, in particular approximately 68°.

Further, the end face 23 or the flow web edge 27 may be inclined obliquely towards one side, in the viewing direction longitudinally of the longitudinal middle axis, for example by an angle W2 of about 3° to 10°, in particular about 5°. This is the angle W3 illustrated in FIG. 1, with which the grip section of the handpiece and/or the outlet channel 26 is upwardly angled with regard to the radial plane to the turbine.

With all exemplary embodiments, the flow web 23 can project over the peripheral wall 5c by an amount e, so that it projects into the free space of the turbine chamber 5 by this amount e. This amount e should be smaller than the radial play for movement between the turbine wheel 4 and the peripheral wall 5c, so that between the turbine wheel 4 and the flow web 23 there is a play for movement.

Below, the functioning of the turbine 3 will be described. In functional operation, the turbine wheel 4 is driven by means of the pressure medium jet flowing secantially through the inlet opening 11a. Thereby, the pressure medium jet is directed between the middle webs 16 and the side wall 5a, whereby an additional torque is transferred to the turbine wheel 4 due to the oblique disposition of the middle webs 16. Further, the middle webs 16 cause the pressure medium to meet the blades 14 on one side, to flow through them axially and then be able to expand in the annular chamber 19, from where—during the rotation in which the pressure medium takes part—it passes into the flow groove 25 arranged with regard to the inlet opening 11a on the other side of the longitudinal middle plane E and then reaches the flow web 23, where the flow obliquely or slightly arc shaped is deflected inwardly past the outlet opening 12a and behind the outlet opening 12a, due to the centrifugal force, again reaches the peripheral wall 5c of the turbine chamber 5. The deflection flow section is illustrated by means of an arrow and designated with 35 in FIGS. 8 to 10. The deflected flow section 35 forms a flow curtain in front of the outlet opening 12a so that exiting of the pressure medium in the turbine chamber 5 through the outlet opening 12a is prevented. As a consequence, no damaging partial vacuum can build up in the turbine chamber 5 which would lead to the undesired sucking-in or sucking-back into the turbine chamber 5. In the functional operation of the turbine 3, i.e. when it is driven with pressure medium under pressure, there builds up in contrast in the turbine chamber 5 such a great pressure that the flow curtain in front of the outlet opening 12 formed by means of the deflected flow section 35 is penetrated and spent pressure medium is continuously discharged.

As can be seen from FIG. 1, the width L2 of the outlet opening 12a is greater than the width d of the annular chamber 19 and, if appropriate, also with the thickness f of the web disk 21. With the present configuration, the dimension L2 is about the half of the axial width g of the turbine chamber 5. The flow recess 25 also has this width. The width g of the annular chamber 19 can, inclusive of the web width f, be about half the width L2 of the outlet opening 12a, or may also be larger.

The prevention of a pump effect in accordance with the invention, upon running on of the turbine wheel 4, takes place both in the upper region of the outlet opening 12a, which lies opposite the annular groove 19 and also in the lower region of the outlet opening 12a, which lies directly opposite the blades 14.

The handpiece 1, the turbine wheel 4 and the bushing 31 are preferably of metal.

In the above description, for reasons of simplification, the term "pressure medium" was used for the overall gas, in particular compressed air, flowing through the turbine 3. Attention is directed to the fact that this actually applies only to the driving pressure medium jet, since the pressure present in the exiting gas is only slightly greater than the atmospheric pressure and is therefore hardly a "pressure medium". For reasons of simplification, however, the employment of the term "pressure medium" is justified overall.

What is claimed is:

1. Turbine handpiece having a drive shaft rotatably mounted in a forward end region of the handpiece, with which a tool can be connected by means of a mounting device, a turbine wheel in a turbine chamber disposed on the drive shaft and fixed for rotation therewith, a delivery line for a flowing pressure medium opening in said turbine chamber at an inlet opening therein and a discharge line extending from said turbine chamber at an outlet opening thereof, means for preventing release of the pressure medium rotating in the turbine chamber through the discharge line after switching off of a supply of the pressure medium during rotation of the turbine wheel, wherein the means for preventing release is disposed in the region of the turbine chamber such that in functional operation said means for preventing release of the pressure medium deflects the pressure medium rotating in the turbine chamber past the outlet opening.

2. Handpiece according to claim 1, wherein the means for preventing release of the pressure medium deflects the flow secantially past the outlet opening.

3. Handpiece according to claim 1, wherein the means for preventing release of the pressure medium has a flow web which projects into the flow of the rotating pressure medium and in functional operation forms a flow step for the rotating pressure medium.

4. Handpiece according to claim 3, wherein the flow web is disposed in the region of a first—with reference to the direction of rotation of the rotating pressure medium—edge of the outlet opening.

5. Handpiece according to claim 3, wherein the flow web extends secantially with regard to the discharge line.

6. Handpiece according to claim 3, wherein a flow groove extending in the direction of rotation is disposed before the flow web.

7. Handpiece according to claim 6, wherein the flow groove runs out at the flow web with an oblique or concavely rounded deflection surface.

8. Handpiece according to claim 6, wherein the flow groove has a rounded or right-angled cross-sectional form.

9. Handpiece according to claim 8, wherein the flow groove has rounded corners.

10. Handpiece according to claim 6, wherein the flow groove has a depth that continuously increases up to the deflection surface.

11. Handpiece according to claim 3, wherein the flow web is disposed at a bushing positioned in the discharge line.

12. Handpiece according to claim 1, wherein the inlet opening is axially off-set with regard to a radial middle plane of the turbine chamber.

13. Handpiece according to claim 1, wherein the outlet opening, longitudinally of the axis of rotation, is offset towards one side of the turbine chamber.

14. Handpiece according to claim 13, wherein the turbine wheel has an annular chamber lying opposite the outlet opening.

15. Handpiece according to claim 14, wherein a dimension of the outlet opening directed longitudinally of the axis of rotation is approximately the same as or greater than the width of the annular chamber.

16. Handpiece according to claim 13, wherein the outlet opening is offset towards the side of the turbine chamber opposite to the inlet opening.

17. Handpiece according to claim 1, wherein the outlet opening is an elongate hole extending longitudinally in a peripheral direction.

18. Handpiece according to claim 1, wherein with regard to a radial middle plane of the turbine chamber, the inlet opening is offset towards one side, and the blades of the turbine wheel are bounded on this side by the oppositely lying side wall of the turbine chamber, with play for movement, and are positioned to direct the pressure medium axially to the other side into an annular chamber which lies radially opposite the outlet opening.

* * * * *